(12) United States Patent
Dea

(10) Patent No.: US 8,739,799 B2
(45) Date of Patent: *Jun. 3, 2014

(54) NON-CONTACT ELECTRONIC TOOL FOR DREAM ENHANCEMENT

(76) Inventor: Jack Y Dea, San Diego, CA (US)

( * ) Notice: Subject to any disclaimer, the term of this patent is extended or adjusted under 35 U.S.C. 154(b) by 232 days.

This patent is subject to a terminal disclaimer.

(21) Appl. No.: 13/176,505

(22) Filed: Jul. 5, 2011

(65) Prior Publication Data

US 2013/0012762 A1   Jan. 10, 2013

(51) Int. Cl.
*A61B 19/00*   (2006.01)

(52) U.S. Cl.
USPC .............................................. 128/897; 600/26

(58) Field of Classification Search
CPC ............... A61M 21/00; A61M 21/02; A61M 2021/0055
USPC ................. 128/897, 898, 899; 600/13, 26, 9; 211/85.2
See application file for complete search history.

(56) References Cited

U.S. PATENT DOCUMENTS

| 5,057,095 A * | 10/1991 | Fabian ............................ 604/362 |
| 5,725,471 A * | 3/1998 | Davey et al. .................... 600/13 |
| 6,048,301 A * | 4/2000 | Sabuda ............................. 600/9 |
| 7,257,967 B2 * | 8/2007 | Rheinstein ........................ 63/40 |
| 7,613,523 B2 * | 11/2009 | Eggers et al. .................. 607/103 |
| 7,824,324 B2 * | 11/2010 | Riehl et al. ......................... 600/9 |
| 7,988,613 B2 * | 8/2011 | Becker ............................ 600/14 |
| 2005/0081561 A1 * | 4/2005 | Eggleston ........................ 63/21 |
| 2007/0234757 A1 * | 10/2007 | Sherman ........................... 63/18 |
| 2009/0100866 A1 * | 4/2009 | Creel ............................. 63/1.11 |
| 2010/0130945 A1 * | 5/2010 | Laniado et al. ............... 604/290 |

* cited by examiner

*Primary Examiner* — Jacqueline Cheng
*Assistant Examiner* — Eileen Foley
(74) *Attorney, Agent, or Firm* — Excelsior Patent Group; Bruce Hare

(57) ABSTRACT

This invention pertains to a non-contact electronic device for the enhancement of dreaming. By enhancement it is meant increasing the frequency, the length, the lucidity, and the color of dreaming. For example, one person who dreams in grey shades now dreams in color when using the device. The device will also allow better recall of the dreams. Dream enhancement is generally a pleasant process and promotes a pleasant feeling in the morning after use. The device is a passive electronic device, that is, it is not actively powered. The user places the device a few feet away during sleep. The device uses a piezo-crystal and an iron core. It is believed that ambient fluctuations in the piezo-crystal's voltage produce an influence field that is broadcasted through the iron core to the user a few feet away.

9 Claims, 3 Drawing Sheets

NON-CONTACT ELECTRONIC TOOL FOR DREAM ENHANCEMENT

FIELD OF THE INVENTION

The present invention relates to the technology of non-contact dream enhancement using electronic components. It uses an iron core driven by the voltage fluctuations of a piezo-crystal. No battery or power source is used. An influence field of around six feet surrounds the device. A person within the influence field will experience enhancement of dreams.

BACKGROUND OF THE INVENTION

The field of dream enhancement usually concerns one of two methods: (1) The use of herbs and vitamins such as vitamin B6 and melatonin, and (2) The use of hypnotic suggestions given by a tape recording. There are drawbacks associated with either of these methods. With herbs and vitamins, there is a possibility that they don't work with everyone who takes them or that it takes many doses before effects take place. There are also the negative effects of side effects on some people. Some side effects include sleeplessness, addiction, LSD effects, and nervous system effects. With CD and taped instructions the major drawback is that they takes time to work if they work at all. In addition, it is quite a nuisance for some people to have to set up and run playback equipment next to their bed when they are already tired and sleepy. Hence, there is a need for a faster, more convenient, and less side effects method for the enhancement of dreams.

Originally, the inventor was developing devices that are able to simulate low frequency fields that often are observed preceding the occurrence of large earthquakes. The magnetic fields were produced from large coils. The electric fields were produced by a large iron ring core with toroidal windings. It was found that a quartz tuning crystal connected to the wiring of the toroid was able to stimulate dreaming. Refining the device to a passive device consisting of iron core, toroidal winded wiring, on-off switch, and quartz crystal, the device is able to generate a field which is used to stimulate lucid dreaming.

One embodiment of the dream enhancement device is capable of producing an influence field of around six feet from the device. That is, the influence field of the device placed in the center of a twelve foot by twelve foot room will influence everybody in the room. One embodiment of the device is composed of a twenty-three inch by eighteen inch rectangular iron core, wiring, and a quartz crystal. Another embodiment of the device uses a two foot diameter iron ring core. A larger iron core is used to generate a stronger influence field.

BRIEF DESCRIPTION OF THE DRAWINGS

The novel features of the invention are set forth in the appended claims. However, for purpose of explanation, several embodiments of the invention are set forth in the following drawings.

DETAILED DESCRIPTION

This invention pertains to a non-contact device that enhances a sleeper's dreaming. The device includes an iron core or other ferro-magnetic core, wiring and a piezo-crystal. The core is typically an iron ring core of a diameter of one to two feet. Square and rectangular cores have also been used successfully.

Figure 1:
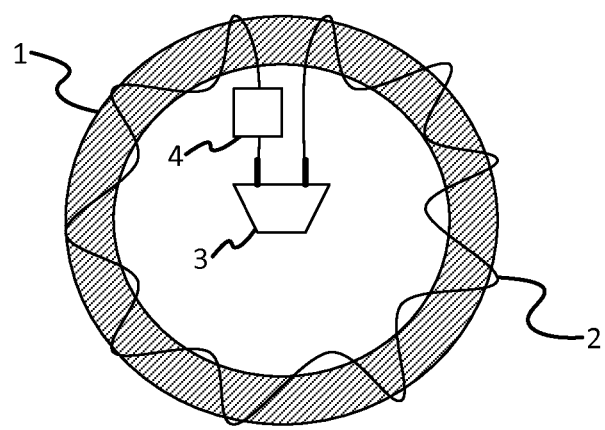
FIG. 1 shows an embodiment of the dream enhancement device with a round iron core.
Figure 2:
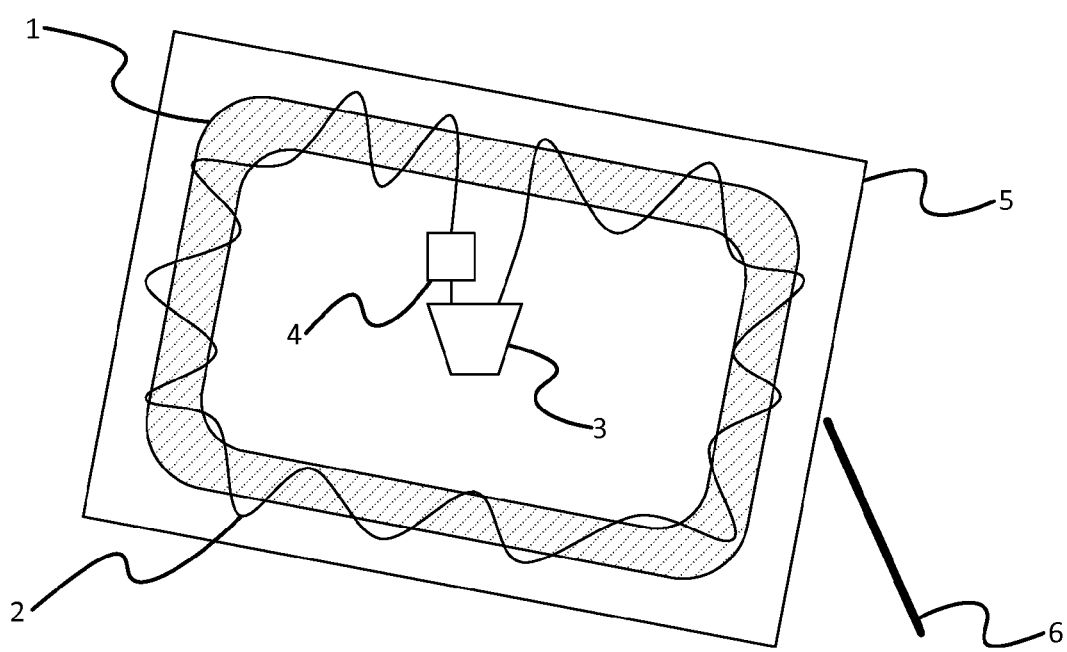
FIG. 2 shows an embodiment of the dream enhancement tool with a rectangular iron core.
Figure 3:
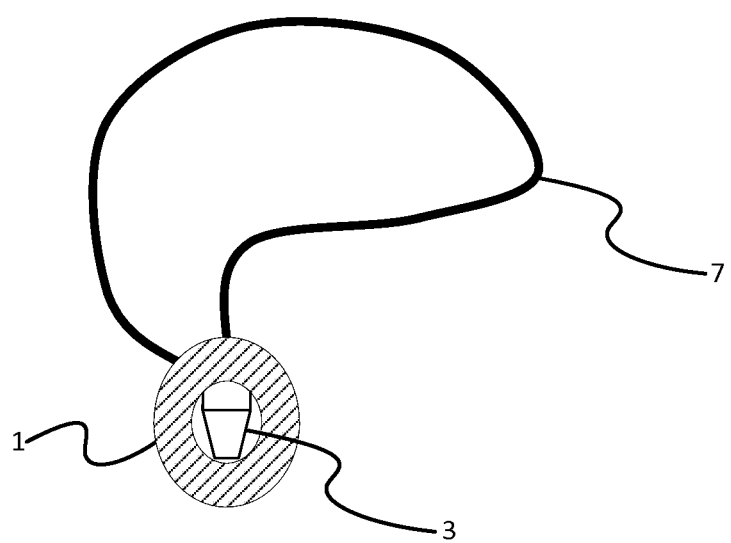
FIG. 3 shows an embodiment of the dream enhancement device in a necklace pendant style.

FIG. 1 shows the parts and connections of the invention. The iron core 1 is wrapped in a toroidal fashion by wire 2. Typically, one turn of wire is winded per inch of core. However, the number of turns of wire is not critical. A piezo-crystal 3, with two conducting surfaces and two leads, is connected to the wire 2, by soldering. A quartz crystal is typically used as the piezo-crystal. An on-off SPST switch 4, connects the wire to one lead of the crystal. In the "off" position, the circuit is open. In the "on" position, the circuit is closed. The quartz crystal 3, can be obtained from electronic supply sources. The wire 2, and on-off switch 4, can also be obtained from electronic supply sources. The iron core 1, can be obtained from specialty metal shops. In FIG. 2, the iron core 1, is rectangular in shape, the dream enhancement system is attached to a frame 5, and the frame is held up by a wire stand 6. In FIG. 3, the dream enhancement device is made into a necklace pendant style. The necklace 7, is worn around the wearer's neck.

In operation, the dream enhancement device is placed a few feet from the head of the sleeper. The positioning is not critical. For example, the dream enhancement device can be laid flat on a chair a few feet from the head of the sleeper or the dream enhancement device can be placed vertically on a chair a few feet from the head of the sleeper. The dream enhancement device can be placed near the top of the head or a few feet on the side of the person. Before the user goes to sleep the device is turned on. The strong influence field from the dream enhancement device is sufficient to affect the sleeper no matter the exact positioning of the device as long as the device is placed near the upper part of the body. Placing the dream enhancement device near the feet of the sleeper does reduce its effectiveness somewhat but the device still functions at a slightly reduced level.

The longer the device is used to stimulate a sleeper, the longer it takes for the sleeper to return to their normal sleep state after the device is turned off. This hysteretic effect may last for several days.

I claim:

1. A non-contact system for use in dream enhancement, the system consisting of:
   an on-off switch;
   a ferro-magnetic core with toroidal wire winding; and
   a piezo-crystal placed inside an opening of the ferro-magnetic core, wherein one end of the winding is terminated at one lead of the piezo-crystal, another end of the winding is terminated at one terminal of the on-off switch, and another lead of the piezo-crystal is terminated at another terminal of the on-off switch, and wherein the system is adapted to generate an influence field capable of enhancing the dream activity of a person within the influence field if the on-off switch is on.

2. The system of claim 1, wherein the ferro-magnetic core comprises iron.

3. The system of claim 1, wherein the piezo-crystal is a quartz crystal.

4. A non-contact system used for dream enhancement, the system consisting of:
   an on-off switch;
   a ferro-magnetic core with toroidal wire winding; and
   a piezo-crystal placed inside an opening of the ferro-magnetic core, wherein one end of the winding is terminated at one lead of the piezo-crystal, another end of the winding is terminated at one terminal of the on-off switch, and another lead of the piezo-crystal is terminated at another terminal of the on-off switch, wherein the core, winding, on-off switch, and piezo-crystal are encased in an enclosure and held upright with a stand, and wherein the system is adapted to generate an influence field capable of enhancing the dream activity of a person within the influence field if the on-off switch is on.

5. The system of claim 4, wherein the enclosure comprises hard plastic.

6. The system of claim 4, wherein the stand comprise metal.

7. The system of claim 4 wherein the ferro-magnetic core comprises iron.

8. The system of claim 4 wherein the piezo-crystal is a quartz crystal.

9. A process adapted to enhance dream activity, the process comprising:
   coupling a ferro-magnetic core with toroidal wire winding to a piezo-crystal, wherein two ends of the winding are terminated at two leads of the piezo-crystal;
   placing the piezo-crystal inside an opening of the core; and
   placing the core and the piezo-crystal in proximity to a sleeping location.

\* \* \* \* \*